United States Patent
Li et al.

(10) Patent No.: US 10,785,720 B2
(45) Date of Patent: Sep. 22, 2020

(54) MEDICAL DEVICE WITH CONTROL CIRCUITRY TO IMPROVE COMMUNICATION QUALITY

(71) Applicant: Pacesetter, Inc., Sylmar, CA (US)

(72) Inventors: Perry Li, Arcadia, CA (US); Lequan Zhang, La Crescenta, CA (US); Xing Pei, Thousand Oaks, CA (US); Jeffery Crook, Belmont, CA (US); Yongjian Wu, Saratoga, CA (US); Jun Yang, Valencia, CA (US); Chao-Wen Young, Cupertino, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 16/743,109

(22) Filed: Jan. 15, 2020

(65) Prior Publication Data

US 2020/0236620 A1 Jul. 23, 2020

Related U.S. Application Data

(63) Continuation of application No. 16/255,178, filed on Jan. 23, 2019, now abandoned.

(51) Int. Cl.
*H04W 52/02* (2009.01)
*H04W 4/80* (2018.01)
(Continued)

(52) U.S. Cl.
CPC ......... *H04W 52/0209* (2013.01); *A61B 5/002* (2013.01); *A61N 1/37223* (2013.01);
(Continued)

(58) Field of Classification Search
None
See application file for complete search history.

(56) References Cited

U.S. PATENT DOCUMENTS

| 8,391,980 B2* | 3/2013 | Bornzin | A61N 1/37 607/27 |
| 8,831,747 B1* | 9/2014 | Min | A61N 1/3756 607/117 |

(Continued)

FOREIGN PATENT DOCUMENTS

WO 2018160442 A1 9/2018

OTHER PUBLICATIONS

International Search Report and Written Opinion for corresponding PCT Application No. PCT/US2020/013790 dated Jun. 24, 2020 (16 pages).

*Primary Examiner* — Thomas S McCormack
(74) *Attorney, Agent, or Firm* — The Small Patent Law Group LLC; Dean D. Small

(57) ABSTRACT

A method for managing power during communication with an implantable medical device, including establishing a communications link, utilizing a power corresponding to a session start power, to initiate a current session between an implantable medical device (IMD) and external device. A telemetry break condition of the communications link is monitored during the current session. The power utilized by the IMD is adjusted between low and high power levels, during the current session based on the telemetry break condition. The number of sessions is counted, including the current session and one or more prior sessions, in which the IMD utilized the higher power level, and a level for the session start power to be utilized to initiate a next session following the current session is adaptively learned based on the counting of the number of sessions.

20 Claims, 5 Drawing Sheets

(51) Int. Cl.
*G16H 40/40* (2018.01)
*A61N 1/372* (2006.01)
*H04Q 9/00* (2006.01)
*A61B 5/00* (2006.01)

(52) U.S. Cl.
CPC ............... *G16H 40/40* (2018.01); *H04Q 9/00* (2013.01); *H04W 4/80* (2018.02); *H04Q 2209/43* (2013.01); *H04Q 2209/883* (2013.01)

(56) References Cited

U.S. PATENT DOCUMENTS

| | | | |
|---|---|---|---|
| 9,044,610 B2 * | 6/2015 | Rosenberg | A61N 1/36071 |
| 9,216,285 B1 * | 12/2015 | Boling | A61N 1/059 |
| 9,232,485 B2 * | 1/2016 | Wu | H04W 52/42 |
| 9,333,351 B2 * | 5/2016 | Arnold | A61N 1/3611 |
| 9,949,660 B2 * | 4/2018 | Weinberg | A61B 5/0452 |
| 2011/0046698 A1 | 2/2011 | Kivi et al. | |
| 2017/0216611 A1 | 8/2017 | Yoder et al. | |

* cited by examiner

MEDICAL DEVICE WITH CONTROL CIRCUITRY TO IMPROVE COMMUNICATION QUALITY

REFERENCE TO RELATED APPLICATIONS

The present application is a continuation application of, and claims priority to, U.S. application Ser. No. 16/255,178, Titled "MEDICAL DEVICE WITH CONTROL CIRCUITRY TO IMPROVE COMMUNICATION QUALITY" which was filed on Jan. 23, 2019, the complete subject matter of which is expressly incorporated herein by reference in its entirety.

BACKGROUND

Embodiments of the present disclosure generally relate to medical devices with control circuitry to improve communication quality while minimizing battery consumption.

An implantable medical device (IMD) is a medical device that is configured to be implanted within a patient anatomy and commonly employs one or more electrodes that either receive or deliver voltage, current or other electromagnetic pulses from or to an organ or tissue for diagnostic or therapeutic purposes. In general, IMDs include a battery, electronic circuitry, a pulse generator, a transceiver and/or a microprocessor that is configured to handle communication with an external instrument as well as control patient therapy. The IMD is completely enclosed within the human body. Thus, there is no means of direct interaction with an IMD, other than through wireless communication.

However, IMDs are typically built with non-replaceable batteries that limit options for communications solutions. Typically, the wireless communication is maintained utilizing a low range, low power communications platform during short periods of time. Existing communication solutions experience certain limitations regarding power consumption. For example, in some environments, current consumption or, more generally, energy usage during communication remains a concern in the IMD. For a Bluetooth Low Energy (BLE) enabled IMD, current consumption by the IMD during advertising is particularly of interest as energy usage during advertising can significantly impact the IMD battery longevity.

A need remains for improved methods and devices for establishing minimizing battery consumption and energy while still providing a quality communication link to external instruments.

BRIEF SUMMARY

A method for managing power during communication with an implantable medical device, including establishing a communications link, utilizing a power corresponding to a session start power, to initiate a current session between an implantable medical device (IMD) and external device. A telemetry break condition of the communications link is monitored during the current session. The power utilized by the IMD is adjusted between low and high power levels, during the current session based on the telemetry break condition. The number of sessions is counted, including the current session and one or more prior sessions, in which the IMD utilized the higher power level, and a level for the session start power to be utilized to initiate a next session following the current session is adaptively learned based on the counting of the number of sessions.

Optionally, the monitoring the telemetry break condition includes counting at least one of a number of return errors or a number of bad packets received by the IMD. Alternatively, adjusting the power comprises changing from the low power level to the high power level during the current session in response to the telemetry break condition indicating an actual or potential telemetry break. In one example, the telemetry break condition indicates the potential telemetry break is based on a measured signal to noise ratio during the session.

In one aspect, the method also includes determining an in-session power transition occurs from the low power level to the high power level, and in response thereto, incrementing the count of the number of sessions in which the IMD utilized the high power level. In another aspect the method includes determining if the count of the number of sessions in which the IMD utilized the high power level has reached a threshold value; and in response to reaching the threshold value, decreasing the power utilized by the IMD during the next session.

Optionally, the monitoring the telemetry break condition includes determining no return errors or bad packets were received by the IMD during the session. In another aspect, responsive to determining no return errors or bad packets are received by the IMD during the session, the method includes decrementing the count of the of the number of sessions in which the IMD is utilizing the high power level. Specifically, adjusting the power comprises changing from the high power level to the low power level for the next session in response to starting a pre-determine amount of sessions at the high power level.

In another aspect, establishing a communications link, utilizing a power corresponding to a session start power, to initiate a current session between an implantable medical device (IMD) and external device includes broadcasting an advertisement message during an interval and transitioning into a sleep mode when a connection is not established during the interval.

In another example, a system for managing power during communication with an implantable medical device, is provided that includes one or more processors configured to execute instructions to establish a communications link, utilizing a power corresponding to a session start power, to initiate a current session between an implantable medical device (IMD) and external device, and monitor a telemetry break condition of the communications link during the current session. The one or more processors also adjust the power utilized by the IMD, between low and high power levels, during the current session based on the telemetry break condition, count a number of sessions, including the current session and one or more prior sessions, in which the IMD utilized the higher power level, and adaptively learn a level for the session start power to be utilized to initiate a next session following the current session based on the counting of the number of sessions.

Optionally, the one or more processors are further configured to execute instructions to monitor the telemetry break condition by counting at least one of a number of return errors or a number of bad packets received by the IMD. In another aspect, the one or more processors are further configured to execute instructions to adjust the power by changing from the low power level to the high power level during the current session in response to the telemetry break condition indicating an actual or potential telemetry break. Optionally, the telemetry break condition indicates the potential telemetry break is based on a measured signal to noise ratio during the session. In an example, the one or more processors are further configured to execute instructions to determine an in-session power transition occurs from the low power level to the high power level, and in response thereto, increment the count of the number of sessions in which the IMD utilized the high power level. In another aspect, the one or more processors are further configured to execute instructions to: determine if the count of the number of sessions in which the IMD utilized the high power level has reached a threshold value; and in response to reaching the threshold value, decrease the power utilized by the IMD during the next session.

In one aspect, the one or more processors are further configured to execute instructions to monitor the telemetry break condition by determining no return errors or bad packets were received by the IMD during the session. Optionally, the one or more processors are further configured to execute instructions to: responsive to determining no return errors or bad packets are received by the IMD during the session, decrement the count of the of the number of sessions in which the IMD is utilized the high power level. Additionally, the one or more processors are configured to execute instructions to adjust the power comprises changing from the high power level to the low power level for the next session in response to starting a pre-determine amount of sessions at the high power level.

In another example, the one or more processors are further configured to execute instructions to establish a communications link, utilize a power corresponding to a session start power, to initiate a current session between an implantable medical device (IMD) and external device by broadcasting an advertisement message during an interval and transitioning into a sleep mode when a connection is not established during the interval.

DETAILED DESCRIPTION

Figure 1:
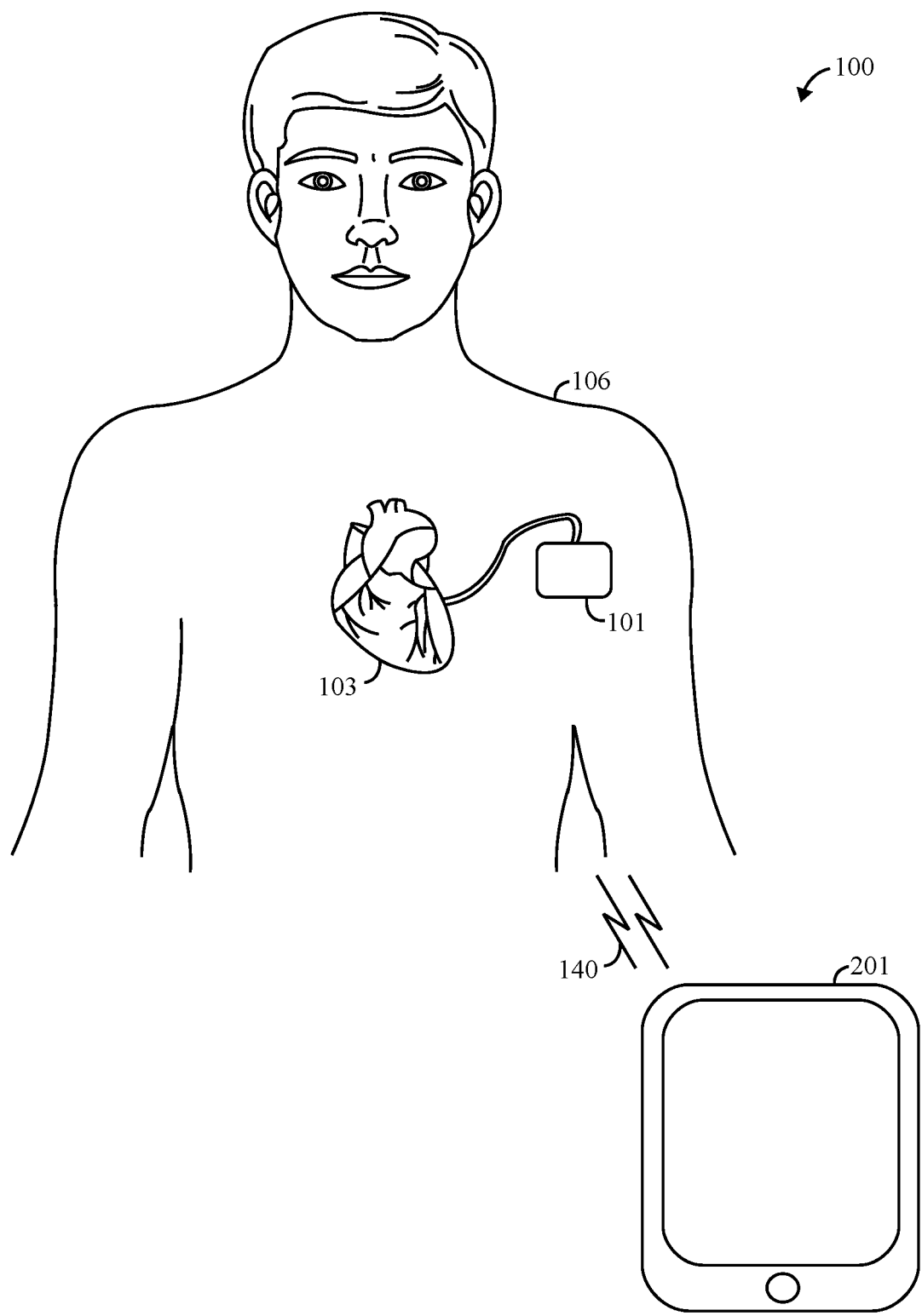
FIG. 1 illustrates a simplified block diagram of a communication system operated in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Provided is a power management system and scheme for wireless communications, such as BLE communications, that decreases battery consumption while optimizing radio frequency (RF) performance. Under current power management schemes, the signal power level is set to a value high enough to achieve minimum required communication range. In one example, the signal power level is set to less than the maximum power possible from the wireless communication device, that in an example is a BLE chip. Once this signal power is set, it never changes throughout the lifetime of the device. As a result, when operating in environments with significant RF interference, the device experiences communication difficulties such as actual telemetry breaks, potential telemetry breaks, telemetry break conditions, dropped communication signals, static, poor sound quality, and the like.

While increasing the signal power may improve chances of connecting to an external instrument, or device, this also results in wasted energy when such increased signal power is unneeded. Specifically, when BLE communications are not being used, which is most of the time, the IMD cannot decrease the signal power during an advertising mode or data transfer to save battery life. This inefficient use of battery leads to other consequences such as the need for longer advertisement periods (1-4 minutes, which leads to long delay before a successful connection) in order to meet longevity requirements or have a direct impact on longevity.

Therefore, the communication system provided recognizes the communication environment surrounding the IMD. As an example, the IMD recognizes when the communication system is being used, and during those times, such as during an in clinic visit, during a scheduled remote care follow-up, or during a patient initiated follow up, can increase the signal power level if the environment is noisy to improve the wireless connection and communication. Meanwhile, when communication is not active, and/or the environment is not noisy, the signal returns to a lower, or low, power level to decrease battery consumption and improve longevity.

The term "actual telemetry break", as used herein, refers to a condition in which a communications link has at least temporarily ended due to one or more of return errors and/or bad packets received by an IMD.

The term "potential telemetry break", as used herein, refers to a condition in which a communications link is maintained, but experiences a number of return errors and/or bad packets received by an IMD in excess of a threshold, thereby indicating a high likelihood that the communications link is about to end.

The term "telemetry break condition", as used herein, refers to a condition of a communications link with respect to an actual or potential telemetry break.

The terms "low power" and "high power", as used herein, do not refer to absolute power levels, but instead referred to power levels relative to one another.

FIG. 1 illustrates a simplified block diagram of a system 100 operated in accordance with embodiments herein. The system 100 includes one or more IMD 101 and one or more external instrument (EI) 201 (e.g., table computer, smart phone, smart watch, laptop, and/or the like) that are configured to communicate with one another wirelessly over a communications link 140.

The IMD 101 is implanted within a patient 106 (e.g., proximate to and/or within a heart 103, proximate to the spinal cord). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference. Additionally or alternatively, the IMD 101 may be a leadless monitor, examples of which are disclosed in U.S. patent application Ser. No. 15/084,373, filed Mar. 29, 2016, entitled, "METHOD AND SYSTEM TO DISCRIMINATE RHYTHM PATTERNS IN CARDIAC ACTIVITY," which is expressly incorporated herein by reference.

Figure 2:
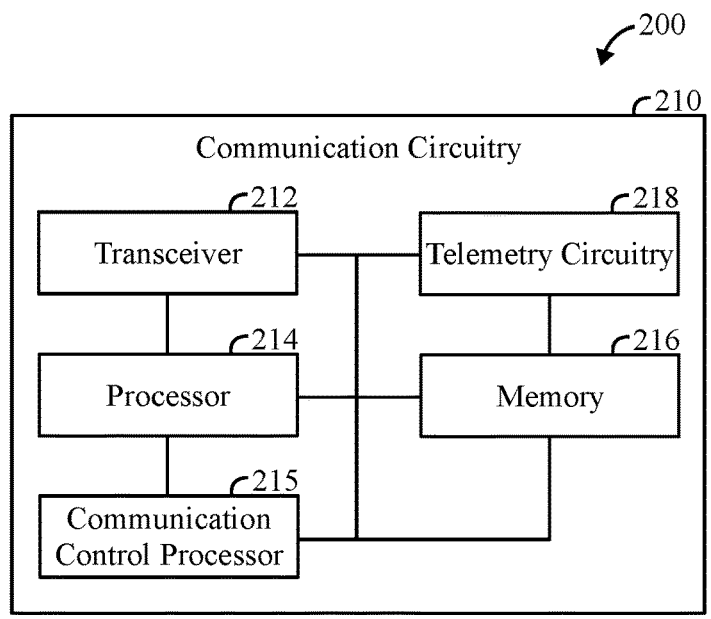
FIG. 2 illustrates a block diagram of communication circuitry operated in accordance with embodiments herein.

FIG. 2 illustrates a block diagram of a communication circuitry 200 of an IMD that in one example is the IMD 101 of FIG. 1. The components described herein can include or represent hardware and software instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. Additionally or alternatively, the components may be hard-wired logic circuits.

The communication circuitry 200 is within the housing 210 of an IMD. The housing 210 is often referred to as the "can", "case" or "case electrode" and may be programmably selected to act as the return electrode for all "unipolar" modes. The housing 210 may further be used as a return electrode alone or in combination with one or more of the coil electrodes for shocking purposes. The housing 210 further includes a connector (not shown) having a plurality of terminals. The terminals may be configured to be coupled to different types of electrodes and leads. In one example embodiment the IMD is a pacemaker.

The communication circuitry 200 is configured to manage the communication link between the IMD 101 and external devices. In one example the communication circuitry 200 may be configured to handle and/or manage the bi-directional communication link 140 between the IMD 101 and the EI 201. In one example the communication circuitry 200 is an RF circuit.

In another example the communication circuitry 200 includes a transponder that transmits signals and a receiver that receives signals. In yet another example, the communication circuitry 200 includes a transceiver 212 (TX/RX) that both transmits signals and receives signals. Specifically, a transceiver includes both a transponder and a receiver. As explained herein, the communication circuitry 200 transmits, among other things, advertising notices in accordance with one or more advertising schedules. The transceiver 212 is tuned to communicate with external devices, including the EI 201 over one or more frequency bands and in accordance with a corresponding protocol. The transceiver 212 may include one or more transmitters/transponders, receivers, and/or transceivers. Optionally, the communication circuitry 200 may be electrically coupled to an antenna (not shown). For example, an antenna may be provided within a header of an IMD as one example. As another example, electrodes on or coupled to the IMD may be utilized to convey the wireless communication signals. The communication circuitry 200 also scans for connection request data packets from external devices. In one example the external device is the EI 201 of FIG. 1.

The communication circuitry 200 also includes one or more processors 214 including a communication control processor 215, a local memory 216, and telemetry circuitry 218, all of which may be implemented on a common circuit board, within a common subsystem or within a common integrated circuit. Specifically, the communication circuitry 200 is in communication with other circuits, components, and modules of the IMD 101 including controller circuit, and IMD local memory 216. The communication control processor 215 may support one or more wireless communication protocols while communicating with an external device such as the EI 201, such as Bluetooth low energy, Bluetooth, Medical Implant Communication Service (MICS), and/or the like.

The memory 216 stores instructions implemented by the communication control processor 215. Protocol firmware may be stored in memory 216, which is accessed by the communication control processor 215. The protocol firmware provides the wireless protocol syntax for the communication control processor 215 to assemble data packets, advertisement notices, connection request data packets, connection responses, establish communication links, such as communication 140, and/or partition data received from an external device, such as EI 201.

The telemetry circuitry 218 in one example monitors the quality of the telemetry or communications link 140. Alternatively, the telemetry software is stored in the memory that provides instructions that are followed by the communication control processor or one or more of the processors 214 related to the communication circuitry 200. The telemetry circuitry 218 in one example determines when the link, and/or how often the link 140 drops causing interruptions in communications being passed through the communications link 140. In another example the telemetry circuitry 218 determines the number of return errors received, number of bad packets received, or the like. Optionally, the telemetry circuitry 218 tracks the signal to noise ratio (RSSI) of the communication link 140. When the communication link 140 is down or not working the telemetry circuitry 218 verifies the power setting of the telemetry link and increases the power setting when a break in the link 140 occurs, or when a link 140 is unable to be established. In this manner, the telemetry circuitry 218 facilitates re-establishment of the link 140 to assist in completing communication sessions. Thus, the telemetry circuitry 218 not only makes determinations regarding when communication breaks occurs including timing to reestablish the link 140 and the like, but additionally, the quality of the telemetry link is determined though various methods including RSSI. The telemetry circuitry 218 also actively corrects any breaks or poor quality communications by increasing power to establish and maintain the link 140.

Figure 3:
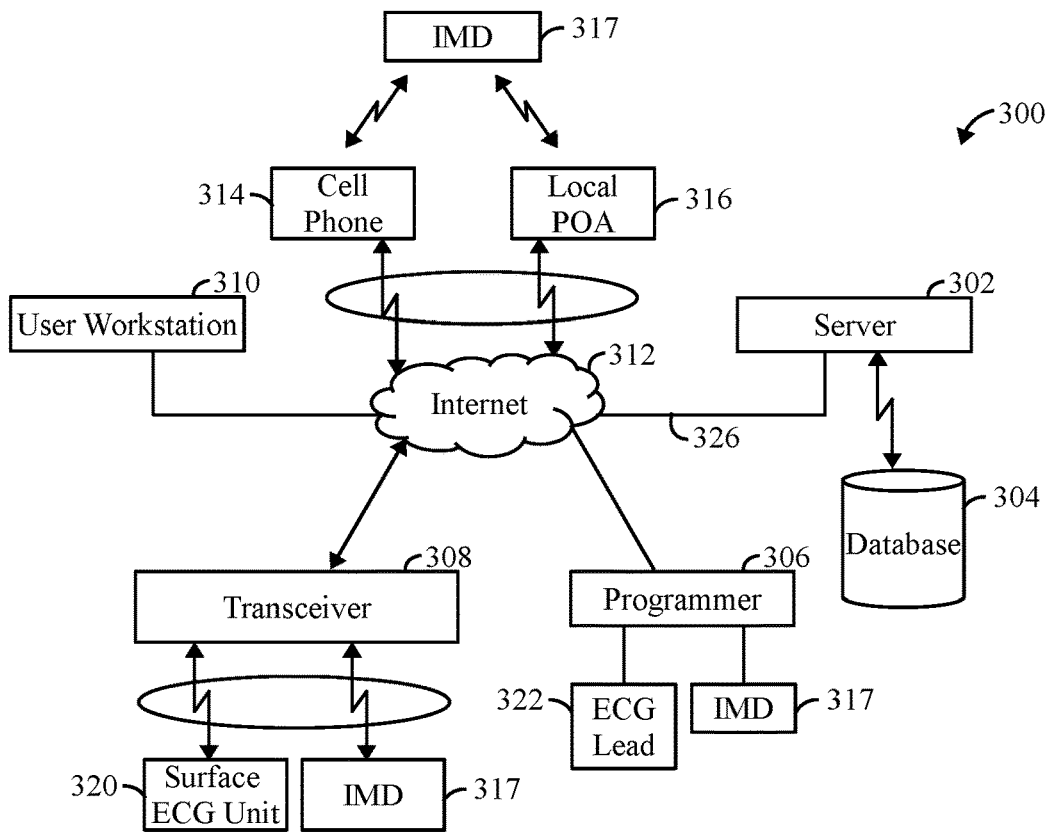
FIG. 3 illustrates a block diagram of an external instrument operated in accordance with embodiments herein.

FIG. 3 illustrates a distributed processing system 300 in accordance with one embodiment. In one example, the distributed processing system 300 includes and implements processes of the communication circuitry 200 as provided in FIG. 2. The distributed processing system 300 includes a server 302 connected to a database 304, a programmer 306, a local RF transceiver 308 and a user workstation 310 electrically connected to a communication system 312. Any of the processor-based components in FIG. 3 (e.g., workstation 310, cell phone 314, PDA 316, server 302, programmer 306, IMD 101) may communicate with an IMD 317 that in one example is IMD 101 of FIG. 1. In one example, the local RF transceiver 308 is the transceiver of 212 of FIG. 2, and the communication system 312 includes communication circuitry 200 of FIG. 2.

The communication system 312 may be the internet, a voice over IP (VoIP) gateway, a local plain old telephone service (POTS) such as a public switched telephone network (PSTN), a cellular phone based network, and the like. Alternatively, the communication system 312 may be a local area network (LAN), a campus area network (CAN), a metropolitan area network (MAN), or a wide area network (WAN). The communication system 312 serves to provide a network that facilitates the transfer/receipt of information such as cardiac signal waveforms, ventricular and atrial heart rates.

The server 302 is a computer system that provides services to other computing systems over a computer network. The server 302 controls the communication of information such as cardiac signal waveforms, ventricular and atrial heart rates, and detection thresholds. The server 302 interfaces with the communication system 312 to transfer information between the programmer 306, the local RF transceiver 308, the user workstation 310 as well as a cell phone 314, a personal data assistant (PDA) 316, and IMD 317 to the database 304 for storage/retrieval of records of information. On the other hand, the server 302 may upload raw cardiac signals from an implanted lead 322, surface ECG unit 320 or the IMD 317 via the local RF transceiver 308 or the programmer 306.

The database 304 stores information such as cardiac signal waveforms, ventricular and atrial heart rates, thresholds, and the like, for a single or multiple patients. The information is downloaded into the database 304 via the server 302 or, alternatively, the information is uploaded to the server from the database 304. The programmer 306 is similar to an external device or instrument and may reside in a patient's home, a hospital, or a physician's office. The programmer 306 interfaces with the lead 322 and the IMD 317. The programmer 306 may wirelessly communicate with the IMD 317 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 306 to the IMD 317. The programmer 306 is able to acquire cardiac signals from the surface of a person (e.g., ECGs), intra-cardiac electrogram (e.g., IEGM) signals from the IMD 317, and/or cardiac signal waveforms, ventricular and atrial heart rates, and detection thresholds from the IMD 317. The programmer 306 interfaces with the communication system 312, either via the internet or via POTS, to upload the information acquired from the surface ECG unit 320, the lead 322 or the IMD 317 to the server 302.

The local RF transceiver 308 interfaces with the communication system 312 to transmit and receive telemetry data and information being transmitted to and from the RF transceiver 308. In one example the communication system monitors the communication link and records telemetry breaks, length of breaks, number of breaks in a given interval, time to reestablish a signal, signal to noise ratio, and the like. In this manner the communication system 312 provides with a user the quality and/or strength of a communication signal and amount or strength of local interference. In addition, the communication system 312 may, based on the monitored communication quality, increase or decrease the power of a signal being transmitted. In one example, the communication system 312 monitors both advertising channels and connection channels, thus providing advertising data packets through and communicating through the advertising channels with external devices such as external instruments. Similarly, the communication system 312 is able to provide a communication pathway through a connection channel.

The user workstation 310 may interface with the communication system 312 to download cardiac signal waveforms, ventricular and atrial heart rates, and detection thresholds via the server 302 from the database 304. Alternatively, the user workstation 310 may download raw data from the surface ECG units 320, lead 322 or IMD 317 via either the programmer 306 or the local RF transceiver 308 or cell phone 314 or PDA 316. Once the user workstation 310 has downloaded the cardiac signal waveforms, ventricular and atrial heart rates, or detection thresholds, the user workstation 310 may process the information in accordance with one or more of the operations described above. The user workstation 310 may download the information and notifications to the cell phone 314, the PDA 316, the local RF transceiver 308, the programmer 306, or to the server 302 to be stored on the database 304. For example, the user workstation 310 may communicate data to the cell phone 314, PDA 316, or IMD 317 via a wireless communication link 326. In one example, the wireless communication link 326 is the communication link 140 of FIG. 1.

Process for Managing Power During Communication

Figure 4:
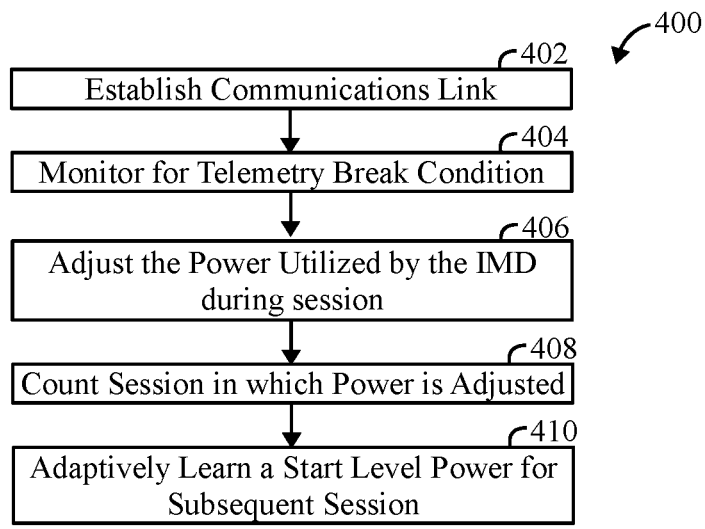
FIG. 4 illustrates a block flow chart of a method in accordance with embodiments herein.

FIG. 4 thus illustrates a flow block diagram of a method 400 for managing power during communication with an implantable medical device (IMD). In one example the IMD is the IMD 101 of FIGS. 1-2. In another example, the IMD includes communication circuitry 200 as provided in FIG. 2. The method 400 may be implemented by hardware components, software components, and/or a combination of hardware components and software components working together to implement the method.

At 402, one or more processors establish a communications link, utilizing a power corresponding to a session start power, to initiate a current session between an IMD and external device. In one example, the communications link is the communications link 140 of FIG. 1. In another example, the communication link utilizes protocols, such as Bluetooth, GSM, infrared wireless LANs, HIPERLAN, 3G, satellite, as well as circuit and packet data protocols, and the like. Alternatively, a hard-wired connection may be used to provide the communications link. In one example, the one or more processors establish the communications link by broadcasting an advertisement message during an interval. Optionally, when a response is not received during the interval to the advertising message, the one or more processors transitions the IMD into a sleep mode, thus saving power.

At 404, one or more processors monitor for a telemetry break condition of the communications link during the current session. In one example, the telemetry break condition is an actual break where communication is lost for a predetermined interval and must be restored or reestablished. The predetermined interval may be a second, less than a second, more than a minute, and the like. In another example, the telemetry break condition is a potential telemetry break. The potential telemetry break is determined based on measured parameters such as signal strength, interference noise level, signal to noise ratio, and the like. In one example a threshold is provided related to one of these parameters, such a signal to noise ratio, that once exceeded, or once falling below the threshold indicates the potential telemetry break is presented. In one example monitoring the telemetry break condition includes determining a number of return errors from sent data packets. In another example, monitoring includes determining the number of bad packets received by the IMD.

At 406, one or more processors adjust the power utilized by the IMD between low and high power levels, during the current session based on the telemetry break condition. In one example the power is adjusted when a pre-existing condition occurs, such as to increase the power from low power to high power during a current session in response to a telemetry break. Alternatively, the power increases from a low power to a high power during a current session when the signal to noise ratio drops below a threshold level during a current session.

At 408, one or more processors counts a number of sessions, including the current session and one or more prior sessions, in which the IMD utilized the higher power level or lower power. In one example, when the one or more processors determine an in-session power transition occurs from the low power level to the high power level, and in response thereto, the one or more processors increment the count of the number of sessions in which the IMD utilized the high power level. The increment can be represented by a numerical value, such as one, another numerical value, or the like. The one or more processors optionally can determine if the count of the number of sessions in which the IMD utilized the high power level has reached a threshold value; and in response to reaching the threshold value, increase the power utilized by the IMD during the next session. In another example, the count increases based on an algorithm or weighted determination. In one example, when the power level is increased because of one preexisting condition such as a telemetry break, a first count amount or score is added to the count, such as two points, whereas when a second preexisting condition such as a signal to noise ratio falling below a threshold amount, a different amount or score is added to the count such as one. Thus, different measured events may result in the same result to the count, such as adding one to a count, or may result in a different result to the count. Similarly, in one example, when the count is increased during consecutive sessions, more weight can be provided to the subsequent consecutive increase. Thus, if power is switched from low to high during a first session, the count increases by 1, but if the power is switched from the low to high power three (3) sessions in a row, the count will increase by 2 as a result of the third consecutive increased session.

At 410, the one or more processors adaptively learn a level for the session start power to be utilized to initiate a next session following the current session based on the counting of the number of sessions. In one example, the one or more processors keep track of the count at 408 and when the count reaches a threshold level, then when a next session begins the one or more processors automatically provide a high power level to start the next session. In one example, the count is 10. In another example the count can increase and decrease. Specifically, in an example when a non-telemetry break condition includes determining no return errors or bad packets were received by the IMD during the session, the count may be decremented. In yet another example, multiple iterations of counts can occur. Specifically, a first count may provide the amount of times a telemetry break occurs during sessions while a second count may provide the amount of times a signal to noise ratio is below a threshold, while yet another count determines the amount of time either a telemetry break or a signal to noise ratio is below the threshold. By keeping track of the count of predetermined events that indicate the interference level in a known environment, the one or more processors are able to adaptively determine the start power for a given environment while keeping power usage low for other environments and uses. Thus, the power usage does not need to remain elevated at times the elevated power level is unneeded. Consequently, power is saved, increasing battery life.

Figure 5:
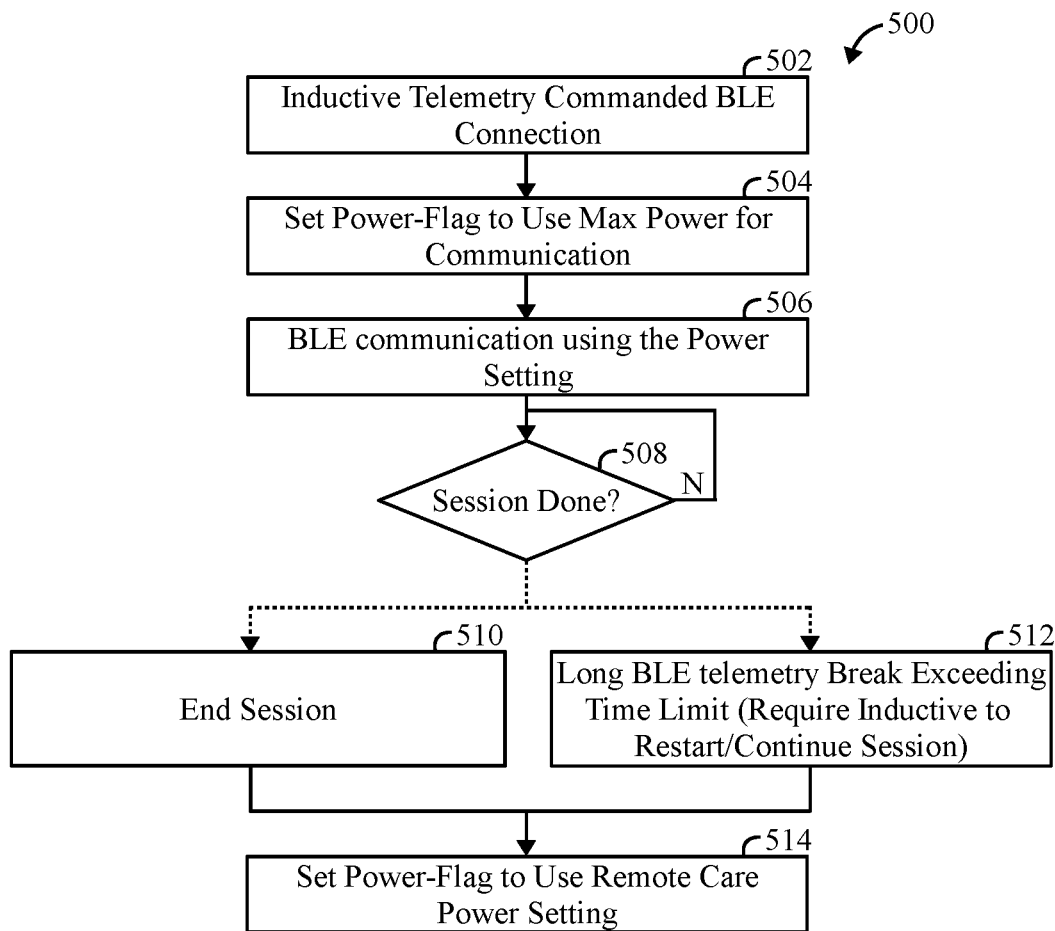
FIG. 5 illustrates a simplified block diagram of a communication system operated in accordance with embodiments herein.
Figure 6:
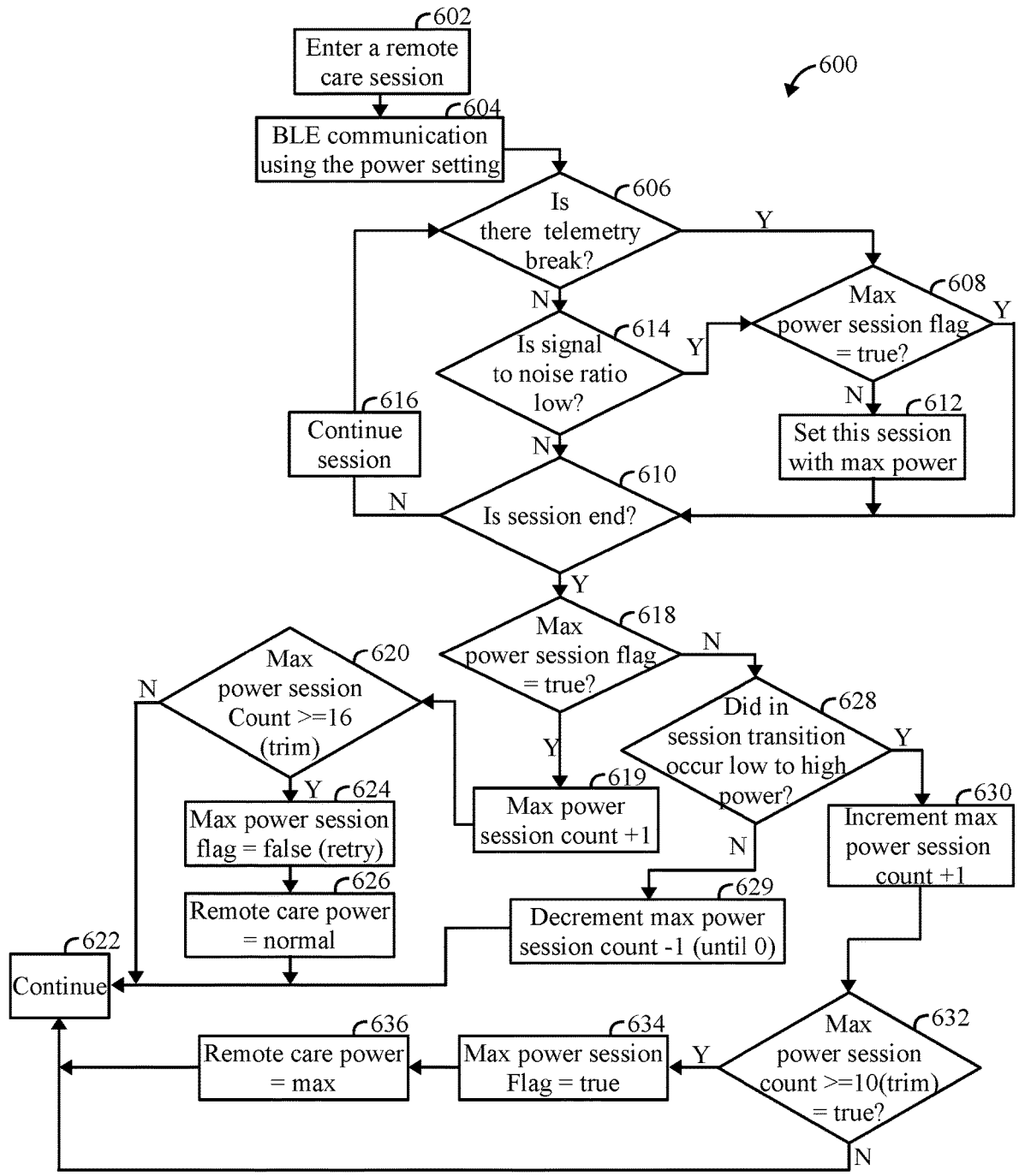
FIG. 6 illustrates a block flow chart of a method in accordance with embodiments herein.

FIGS. 5 and 6 illustrate two common use cases for a power scheme that are user initiated in clinic communication and scheduled remote care monitoring/user initiated remote care transmission. First, for the user initiated in clinic communication use case illustrated in the block flow diagram of FIG. 5, the user initiates the communication with an alternative method such as inductive telemetry. The one or more processors of the IMD set the power-flag of the implant to use maximum power for communication, because the timing demand and uncertainty of operational environment in the in-clinic. In this case, the implant subsequently uses the maximum transmit power to advertise, connect to external devices, and transfer data packets for the connection session. When the session is finished, the one or more processors of the IMD sets the power-flag to a remote care power setting.

Therefore, FIG. 5 illustrates a method 500 for managing power during communication with an IMD. In one example the IMD is the IMD 101 of FIGS. 1-2. In another example, the IMD includes communication circuitry 200 as provided in FIG. 2. The method 500 may be implemented by hardware components, software components, and/or a combination of hardware components and software components working together to implement the method.

At 502, one or more processors based on inductive telemetry command a communication connection. In one example the communication connection is a BLE connection. In one example, a patient with an IMD has a scheduled in-person appointment within an environment, that in this example is a clinic.

At 504, a power-flag is set to use maximum power for communication. In one example, the maximum power is a predetermined level. When used herein a "flag" is utilized as understood in a computer science context and is considered a bit or bit sequence that is used by a program, or one or more processors, to remember or leave a sign for another program for use. In this manner, when the one or more processors operate to determine the power level that should be utilized during a visit or appointment in a pre-determined environment, the processors immediately determine maximum power shall be utilized in the environment. In an example, a program that is not the program that makes the maximum power determination sets the flag and is separate, or a different program than the program that utilizes the flag, or maximum power command in order to begin learning the clinic environment. In other words, for this common use case, when an IMD is to be within a new communications environment, such as a first time within the communications environment of a pre-determined clinic, method 500 provides examples of how the communication circuitry sets its power level to a maximum power setting within such a new environment for the initial visit to provide as much power as possible during an initial communication session. Alternatively, as illustrated and described in relation to FIG. 6, a power flag is not set to have an initial maximum power setting, and thus the system starts at a minimum or low power setting.

At 506, the IMD communicates with an external instrument (EI) using the communication connection. In one example, the communication connection is a BLE connection. In an example, the EI is a monitor that provides medical data related to the IMD and patient based on a communication session through the communication connection. In particular, at this time a patient is within the clinic environment during an appointment and testing is occurring by a clinician. Because the maximum power is being utilized, an optimal communication environment is formed by the IMD to provide optimal medical data from the communication session.

At 508 a decision is made regarding whether the session is done. If not, the communication session continues, and the IMD remains at a maximum power level to continue to provide an optimal communication link for gathering the desired medical data. At 508, in one example the decision made regarding whether a session is done is made in two different manners. In a first determination, a signal, prompt, or the like is provided that the session is complete, ending the session at 510. In such an example the signal, prompt, or the like may be provided by the EI, a remote clinician device such as a computer, tablet, or the like, a remote patient device such as a handheld phone, watch, or the like. Alternatively, at 512, a telemetry break occurs that exceeds a pre-determined time period, or limit. In one example the pre-determined time period is one hour. Specifically, if the EI and IMD do not exchange information, or communicate with one another for an hour, the one or more processors determine the communication session is complete. If the communication session is not complete, the communication session may be restarted through inductive telemetry utilizing methods as previously described.

If at 508, a determination is made that the communication session is done, either through a command 510 or through a session timing out 512, at 514, the power flag is set to a minimum power setting. In one example the minimum power setting is considered a remote care power setting. Again, a bit or bit sequence provides the remote care power setting for the one or more processors of the IMD to utilize in subsequent uses or environments. In this manner, when a maximum power is desired for communication in the clinic environment, a maximum power state is provided, while when not in a clinic environment, a minimum amount of power is provided. Consequently, power consumption is more efficient, power is saved, extending battery life.

The second common use case is for remote care monitoring as illustrated in FIG. 6. In this use case, the one or more processors of the IMD sets a power-flag to use a remote care power setting after it comes out from shipped setting. In other words, instead of the power setting being altered before entering a clinic environment to provide an initial maximum power setting as described in relation to FIG. 5, the power-flag instead remains at a minimum power setting when entering the clinician environment and must self-correct, or adjust to the clinic environment based on active and on-going telemetry quality monitoring. Specifically, the transmit power level is set to low power, the max power session count is set to 0, and the max power session flag is set to false. After the remote care communication session begins, the IMD monitors the quality of the telemetry link. If one telemetry break or number of telemetry breaks occurs, the IMD checks if the max power setting has been used. If yes, it will keep using the max power setting and try to re-establish the link and finish the session. If not, the IMD switches to max power setting and attempts to re-establish the link and finish the session.

If the telemetry doesn't break, the one or more processors also check the quality of the telemetry link through various additional methods, including relative received signal strength (RSSI). In one example the RSSI is determined as provided in methodologies related to IEEE 802.11. Alternatively, return errors and bad data packets are counted. If the quality is deemed too low, the processors of the IMD also set the power level to max. After the session is finished, the one or more processors of the IMD check if the session starts and exits with max power setting. If the session starts as a low power session, but ends in a high power session, a new high power session is provided. The max power session counter therefore increases by 1. When the max power session counter reaches a threshold, the max power session indicates the communication environment is not ideal. The device thus sets the remote care communication power to max power for the next session to increase the successful rate.

In the next session, the remote care session starts with high power, and the IMD increases the max power setting count by 1. If the max session count exceeds a predefined threshold, such as N, the IMD switches the power setting to low power to try low power for the next remote care session. In the next session starting with low power, if the communication is successful, the device will decrease the max power setting count by 1, until 0. If the communication is not successful and device switches to max power, the device will increase the max power setting count by 1 and the subsequent remote care session will start with high power again.

Thus, as illustrated in relation to FIG. 6, a method 600 of managing power during communication with an IMD is provided. In one example the IMD is the IMD 101 of FIGS. 1-2. In another example, the IMD includes communication circuitry 200 as provided in FIG. 2. The method 600 may be implemented by hardware components, software components, and/or a combination of hardware components and software components working together to implement the method.

At 602, the IMD enters a remote care communication session. In one example the communication session is entered in a clinic environment wherein the patient has an appointment for a clinician to monitor the operation of the IMD and health of the patient. The communication session is entered into as a result of the appointment or monitoring. In another example, the remote care communication session is entered into as a result of in home monitoring of a patient.

At 604, the one or more processors begin the communication session at a predetermined power setting. In one example the pre-determined power setting is set at a maximum power level as described in relation to FIG. 5. Alternatively, the power setting is set at a minimum power as a result of a first or initial use of the IMD in the clinic environment. Alternatively, the power setting is set as determined by the one or more processors utilizing the methodology as provided in this method 600 as will be described in full herein.

At 606 a determination is made whether there is a telemetry break condition is provided. In one example the telemetry break condition occurs when a signal is lost resulting in a telemetry break. Alternatively, the potential telemetry break condition is determined based on measured parameters such as signal strength, interference noise level, signal to noise ratio, and the like. In one example a threshold is provided related to one of these parameters, such a signal to noise ratio, that once exceeded, or once falling below the threshold indicates the potential telemetry break is presented. In one example monitoring the telemetry break condition includes determining a number of return errors from sent data packets.

Thus, at 608 if a telemetry break occurs at 606 flow goes to the right and the one or more processors determine if the maximum power flag is set as true. In one example the maximum power flag is set as true as a result of the initial power setting being set at a maximum power as provided in the method of FIG. 5. Alternatively, the maximum power flag is set as true as a result of determination made in this method 600 of FIG. 6.

If at 608 the maximum power flag is set at a maximum power, then the flow goes to the right and the one or more processors determine whether the session has ended at 610. Alternatively, if the maximum power flag is not set at maximum power, then the flow goes down and at 612 the power level is increased. In one example the power level is increase to a maximum power level, thus going from a low power level to a high power level. In another example the power level is increased incrementally to a level higher than the initial power level, but not to a maximum power level. Regardless, after the power level is increased, the determination is made regarding whether the session has ended at 610.

If at 606 a telemetry break has not occurred, then at 614 the one or more processors determine whether a signal to noise ratio is above a predetermined threshold. In one example, the determination is made utilizing RSSI. If the determination is made that the signal to noise ratio has not reached the predetermined threshold, thus indicating a potential for a telemetry break and thus that a telemetry break condition is provide, then flow goes to the right to 608 to determine if the maximum power flag is set to at a maximum power. Thus, flow moves as described above. Alternatively, a number of signal errors, and/or bad data packets are counted to make a similar determination related to the telemetry break condition.

If at 614 the signal to noise ratio is above a predetermined threshold, or other telemetry break condition do not exist, then flow moves downward to 610 for a determination regarding whether the session has ended. Specifically, in this example if a telemetry break condition is not detected and the signal to noise ratio is above a predetermine threshold, a telemetry break condition is not presented. In other examples, additional determinations may be made regarding whether a telemetry break condition is presented and considered during such determinations. Factors related to the telemetry break condition may include the number of return errors, number of bad packets, or the like during a communication session.

If at 610 the session has not ended, then the communication session continues at 616 and the one or more processors continue to attempt to determine if a telemetry break condition is occurring at 606. Importantly, the one or more processors continue to attempt to establish a strong communication path and in examples when the power has been incrementally increased at 612, the increased power level may result in the telemetry break condition from not occurring, resulting in a different outcome and the one or more processors thus learns the power level needed for the given clinical environment.

Once the communication session has ended at 610, flow moves downward to 618 and a determination is made whether a maximum power session flag was originally set to true. In one example, the flag of the communication session is set as true as described in FIG. 5. Alternatively and additionally, the maximum power flag is set at true as a result of this method 600 described herein.

If at 618, the maximum power session flag was set to true, flow moves to the left and the one or more processors increase a max power session count by a predetermined amount at 619. In one example the count is increased by one.

At 620, after the power increases by the predetermined amount, a determination is made regarding whether the count meets or exceeds a predetermined threshold value. In one example the predetermined count is sixteen (16). If the predetermined count does not meet or exceed the threshold value, then flow moves to the left and the method continues at 622 with the initial power setting at a maximum power level.

Alternatively, if at 620 the count meets or exceeds a predetermined threshold value, at 624 the maximum power session flag is set to false and at 626 the remote care power is set to low power. In this example, once a maximum power session flag is determined for 604, the IMD automatically starts at the maximum power level for a predetermined amount of times, in this example sixteen. After the threshold amount of sessions is complete, the one or more processors changes the maximum power session flag to false, thereby resulting in the initial power setting of the next session to be low and the maximum power session count is reset. Therefore, the process forces a retry of the communication environment to make determinations if changes in the communication environment have occurred that result in maximum power use being unneeded. If maximum power is still required, the method works through to increase the power setting to a maximum setting as described herein to ensure the proper power level is provided. Specifically, the count remains the same, such that if power is increased during the subsequent session, the initial maximum power requirement is reinitiated. If the communication environment has changed and maximum power is no longer required, then the system operates with low power in the communication environment, saving power usage and battery life. Thus, after the remote care power is returned to low power at 626 the method continues at 622.

If at 618 the communication session was initiated, and the maximum power session was not set as true, then at 628, the one or more processors determine if an in-session power transition occurs from a low power level to the high power level. In one example, this increase is a local increase, or in other words, the maximum power level of the IMD is not reached, however an incremental increase in power has occurred during the session. For example, if at 612 power is increased, a local maximum power of the IMD is determined as a "Yes", or is determined to be presented, even though the IMD is not at a maximum power for the IMD. Specifically, the one or more processors are attempting to determine when power has to be increased or maximized during a session as a result of a telemetry break condition.

If at 628 the power level was not increased from a low level to a high, or higher level during the session, then flow moves left from 628 and the max power session count is decreased by one (−1) at 629. Specifically, if the power level does not start at a maximum power level and does need to be increased during a session, then a good communication environment is determined and the count to increase the power level initially during a subsequent session is decreased accordingly to prevent an unnecessary increase in power. Then the method continues at 622.

Alternatively, if at 628 the power level did increase from a low power level to a high or higher power level during a session, the incremental maximum power session count is increased by a predetermined amount at 630. In one example the predetermined amount is one (1). In yet another example the count is increased by more than one based on pre-existing conditions. For example, if the power level is increased from an initial power to a higher power for three consecutive sessions, the count in the third consecutive session may increase by two instead of only one. Alternatively, more weight may be provided to increasing to a maximum power level, or otherwise, to increase the count.

After the maximum power count is increased at 630, at 632 a determination is made whether the maximum power session count meets or exceeds a threshold count. In one example the threshold count to 10. If the threshold is not met or exceeded, then the flow moves downward, and the method continues with no change in the initial power setting for a subsequent, or next communication session and the methodology continues at 622. If at 632 the threshold count is met or exceeded, then flow moves left, and the maximum power session flag is changed to true at 634 and the remote care power flag is changed to maximum at 636. Therefore, in one example, if the power in a clinic environment must be increased from low power to high power in ten separate sessions, a poor communication environment is determined, and the initial power setting is maximized for the next communication session to ensure clear communication and data exchange between the IMD and EI. Thus, at this point the methodology continues at 622.

Figure 7:
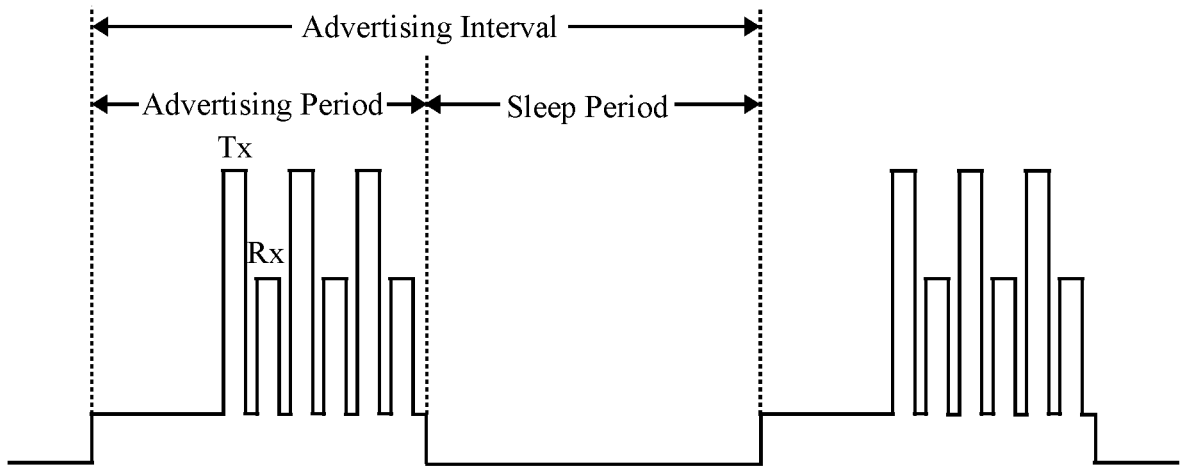
FIG. 7 illustrates a graph of power usage over time in accordance with embodiments herein.

In an example experiment an IMD was set up as a peripheral that broadcasted an advertisement message (Tx) then listened for a response signal (Rx) on each of three advertisement channels occurring at predetermined intervals. During the predetermined intervals the IMD goes into a sleep mode if no connection is established. Such an advertising scheme is illustrated in the graph of FIG. 7. Specifically, the time during advertising is the advertising period while the time the IMD is in sleep mode is a sleep period, while the time between a first advertisement and a second advertisement is an advertising interval.

The calculation of average current over a 5 second advertising interval (Iavg@5s Adv interval) is as follows:

$$Iavg@5\text{ s }Adv\text{ interval} = \frac{(Iadv \times Tadv + Islp \times (5\text{ s} - Tadv))}{5\text{ s}}$$

Where Iady is the advertising current in milli amps (mA), Tadv is the advertisement period in milli seconds (ms), and Islp is the sleep current in nano Amps (nA).

Figure 8:
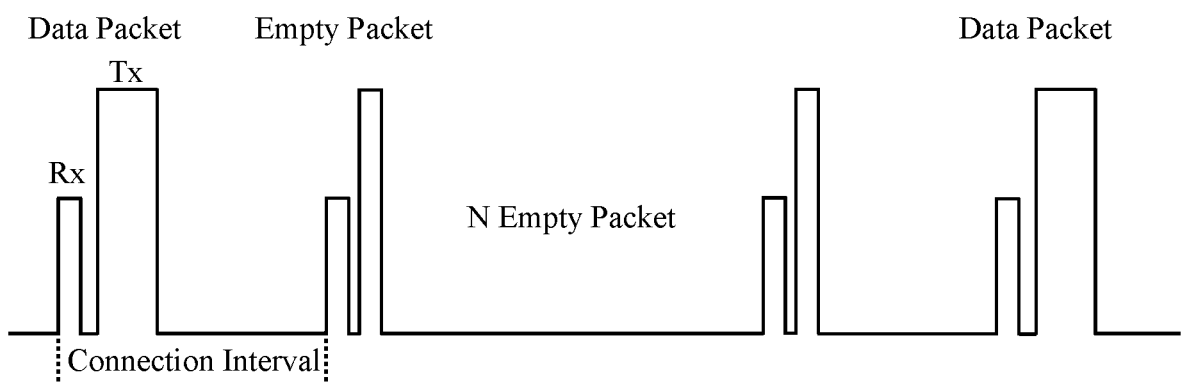
FIG. 8 illustrates a graph of power usage over time in accordance with embodiments herein.

After the IMD is connected to an EI, the IMD continues to transmit empty packets at every connection interval to maintain the communication link as illustrated in the graph of FIG. 8. The data packet may include a payload of up to 255 bytes and is transmitted across the link by the IMD at each connection interval when data is available. Specifically, the IMD comes out of standby or sleep mode to transmit the packet, and then goes to back into standby or sleep mode to wait for a next connection interval. The connection and data transfer process is thusly illustrated in FIG. 8.

Table 1 illustrates a first table with the average current of advertising with a five second advertising interval at 0 dBm (decibels in relation to one milli Watt), 3 dBm, and 6 dBm. Specifically, 3 dBm output power increases a link budget by 3 dB, or extends the communication range by 43%, and by using 6 dBm can increase a link budget by 6 dBm or extend the communication range by 102% and are thus utilized accordingly.

TABLE 1

| Power Level | Average Current (mA) | Current Saving |
|---|---|---|
| 0 dBm | 1.37 | 56.9% |
| 3 dBm | 1.81 | 55.5% |
| 6 dBm | 3.94 | 0% |

Table 2 meanwhile provides a table of the average current and savings of transferring an 80-byte payload packet for various power levels, similarly at 0 dBm, 3 dBm, and 6 dBm.

TABLE 2

| Power Level | Average Current (mA) | Current Saving |
|---|---|---|
| 0 dBm | 3.6 | 68.1% |
| 3 dBm | 5.5 | 50.3% |
| 6 dBm | 11.3 | 0% |

Table 3 meanwhile illustrates the average current and savings of transferring an empty packet for power levels at 0 dBm, 3 dBm, and 6 dBm.

TABLE 3

| Power Level | Average Current (mA) | Current Savings |
|---|---|---|
| 0 dBm | 2.4 | 48.9% |
| 3 dBm | 3.3 | 29.8% |
| 6 dBm | 4.7 | 0% |

The average current of a user scenario of continuously streaming two EGMs (electrograms) is provided in Table 4 below. Specifically, with an assumption of 10 ms connection interval and sending one 80 byte data packet every four connection intervals to achieve a data rate of 2 KB/s, the calculation is provided in Table 4 using the following calculation:

$$Iavg = \frac{Idata \times Tdata + N \times Iempty \times Tempty + Istanby \times ((N+1) \times Tinteval - Tdata - N \times Tempty)}{(N+1) \times Tinterval}$$

Where Iavg is the average current in uA, Idata is the data packet current in mA, Tdata is the data packet period in ms, N is the number of empty packets between data packets in counts, Iempty is the Empty packet current in mA, Tempty is the empty packet period in ms, Istanby is the standby current in uA, and Tinteval is the connection interval in ms. Thus, Table 4 below illustrates the average current and savings streaming two channels of EGM for power levels of 0 dBm, 3 dBm, and 6 dBm.

TABLE 4

| Power Level | Average Current (mA) | Current Saving |
|---|---|---|
| 0 dBm | 1.02 | 55.5% |
| 3 dBm | 1.18 | 48.0% |
| 6 dBm | 2.29 | 0% |

Thus, by utilizing the methodologies herein numerous advantages over other systems and methods are achieved. By utilizing maximum power during communication sessions, a better user experience results including having a more robust communication link, more immunity to ambient interferences, and experience fewer interruptions to the link. By utilizing power switching, the system and methodology allows the device to switch to lower power when the link quality is good or when a communication session is not active. Consequently, power consumption is decreased, resulting in increased IMD life.

Additionally, the method and system may be retrofit into current applications because it is communication IC (integrated chip) independent, or BLE IC independent. Thus, the method and system may be implemented on all such devices including existing devices. Consequently, better connectivity and patient experience is achieved.

CLOSING STATEMENT

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method for managing power during communication with an implantable medical device, the method comprising:
   establishing a communications link, utilizing a power corresponding to a session start power, to initiate a current session between an implantable medical device (IMD) and external device;
   monitoring a telemetry break condition of the communications link during the current session;
   adjusting the power utilized by the IMD, between low and high power levels, during the current session based on the telemetry break condition;
   counting a number of sessions, including the current session and one or more prior sessions, in which the IMD utilized the higher power level; and
   adaptively learning a level for the session start power to be utilized to initiate a next session following the current session based on the counting of the number of sessions.

2. The method of claim 1, wherein the monitoring the telemetry break condition includes counting at least one of a number of return errors or a number of bad packets received by the IMD.

3. The method of claim 1, wherein the adjusting the power comprises changing from the low power level to the high power level during the current session in response to the telemetry break condition indicating an actual or potential telemetry break.

4. The method of claim 3, wherein the telemetry break condition indicates the potential telemetry break is based on a measured signal to noise ratio during the session.

5. The method of claim 1, further comprising determining an in-session power transition occurs from the low power level to the high power level, and in response thereto, incrementing the count of the number of sessions in which the IMD utilized the high power level.

6. The method of claim 5, further comprising determining if the count of the number of sessions in which the IMD utilized the high power level has reached a threshold value; and in response to reaching the threshold value, decreasing the power utilized by the IMD during the next session.

7. The method of claim 1, wherein the monitoring the telemetry break condition includes determining no return errors or bad packets were received by the IMD during the session.

8. The method of claim 7, responsive to determining no return errors or bad packets are received by the IMD during the session, decrementing the count of the of the number of sessions in which the IMD is utilizing the high power level.

9. The method of claim 8, wherein adjusting the power comprises changing from the high power level to the low power level for the next session in response to starting a pre-determine amount of sessions at the high power level.

10. The method of claim 1, wherein establishing a communications link, utilizing a power corresponding to a session start power, to initiate a current session between an implantable medical device (IMD) and external device includes broadcasting an advertisement message during an interval and transitioning into a sleep mode when a connection is not established during the interval.

11. A system for managing power during communication with an implantable medical device, comprising:
    one or more processors configured to execute instructions to:
       establish a communications link, utilizing a power corresponding to a session start power, to initiate a current session between an implantable medical device (IMD) and external device;
       monitor a telemetry break condition of the communications link during the current session;
       adjust the power utilized by the IMD, between low and high power levels, during the current session based on the telemetry break condition;
       count a number of sessions, including the current session and one or more prior sessions, in which the IMD utilized the higher power level; and
       adaptively learn a level for the session start power to be utilized to initiate a next session following the current session based on the counting of the number of sessions.

12. The system of claim 11, wherein the one or more processors are further configured to execute instructions to: monitor the telemetry break condition by counting at least one of a number of return errors or a number of bad packets received by the IMD.

13. The system of claim 11, wherein the one or more processors are further configured to execute instructions to: adjust the power by changing from the low power level to the high power level during the current session in response to the telemetry break condition indicating an actual or potential telemetry break.

14. The system of claim 13, wherein the telemetry break condition indicates the potential telemetry break is based on a measured signal to noise ratio during the session.

15. The system of claim 14, wherein the one or more processors are further configured to execute instructions to: determine an in-session power transition occurs from the low power level to the high power level, and in response thereto, increment the count of the number of sessions in which the IMD utilized the high power level.

16. The system of claim 15, wherein the one or more processors are further configured to execute instructions to: determine if the count of the number of sessions in which the IMD utilized the high power level has reached a threshold value; and in response to reaching the threshold value, decrease the power utilized by the IMD during the next session.

17. The system of claim 11, wherein the one or more processors are further configured to execute instructions to: monitor the telemetry break condition by determining no return errors or bad packets were received by the IMD during the session.

18. The system of claim 17, wherein the one or more processors are further configured to execute instructions to: responsive to determining no return errors or bad packets are received by the IMD during the session, decrement the count of the number of sessions in which the IMD is utilized the high power level.

19. The system of claim 18, wherein the one or more processors are configured to execute instructions to: adjust the power comprises changing from the high power level to the low power level for the next session in response to starting a pre-determine amount of sessions at the high power level.

20. The system of claim 11, wherein the one or more processors are further configured to execute instructions to: establish a communications link, utilize a power corresponding to a session start power, to initiate a current session between an implantable medical device (IMD) and external device by broadcasting an advertisement message during an interval and transitioning into a sleep mode when a connection is not established during the interval.

* * * * *